United States Patent [19]

Laqua et al.

[11] 4,189,311

[45] Feb. 19, 1980

[54] 1,3-DI-N-DECYL-2-METHYL-IMIDAZOLIUM CHLORIDE OR BROMIDE AND MICROBIOCIDAL PREPARATION CONTAINING THIS COMPOUND

[75] Inventors: Arnold Laqua; Ulrich Holtschmidt, both of Essen, Fed. Rep. of Germany

[73] Assignee: Th. Goldschmidt AG, Fed. Rep. of Germany

[21] Appl. No.: 959,020

[22] Filed: Nov. 9, 1978

[30] Foreign Application Priority Data

Jul. 3, 1978 [DE] Fed. Rep. of Germany ....... 2829137

[51] Int. Cl.$^2$ ............................................... A01N 9/22

[52] U.S. Cl. .................................... 71/67; 424/273 R

[58] Field of Search .................................... 424/273 R

[56] References Cited

U.S. PATENT DOCUMENTS 4,062,965  12/1977  Holtschmidt et al. ........... 424/273 R

*Primary Examiner*—V. D. Turner
*Attorney, Agent, or Firm*—James E. Bryan

[57] ABSTRACT

This invention relates to a microbiocidal composition comprising a carrier and a microbiocidally effective amount of 1,3-di-n-decyl-2-methyl-imidazolium chloride or bromide.

2 Claims, No Drawings

1,3-DI-N-DECYL-2-METHYL-IMIDAZOLIUM CHLORIDE OR BROMIDE AND MICROBIOCIDAL PREPARATION CONTAINING THIS COMPOUND

U.S. Pat. No. 4,062,965, relates to quaternary imidazolium salts of the general formula

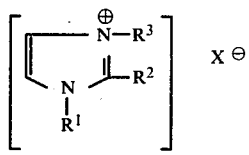
                      I wherein
$R^1$ is a straight-chain alkyl group with 8 to 18 carbon atoms, $R^2$ is a straight-chain alkyl group with 1 to 3 carbon atoms, $R^3$ is a straight-chain alkyl group with 8 to 16 carbon atoms and X is chlorine or bromine.

Also disclosed in the patent is a process for preparing the above compounds by reacting a compound of the general formula

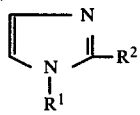
                      II wherein $R^1$ and $R^2$ are the same as in formula I, in known manner in a polar solvent, with at least an equimolar amount of a compound of the general formula $R^3X$, where $R^3$ and X have the meaning indicated in formula I, at temperatures between 80° and 150° C., whereupon the solvent and any excess of $R^3X$ are removed.

Lastly, the above cited patent relates to a microbiocidal preparation composed of one or more compounds of the above formula I and a carrier.

The aforementioned patent explains that the compounds disclosed therein are surprisingly highly effective against bacteria, fungi and yeasts. The compounds are water soluble and therefore can be prepared in a conventional manner. The term preparation here means the making of applicable substances, for instance aqueous solutions of the compounds of the invention in concentrated form or at typically appropriate concentrations. Therefore the preparation also includes the setting of a specific pH value corresponding to the particular application and possibly also the addition of cationic or non-ionic known surfactants to reduce the boundary surface tension of the solutions and/or to increase their cleansing effect, possibly also to obtain coloration and/or scenting of the substance. Another form of preparation is in making a dry product by using the crystalline pure substance or by mixing the pure substance with especially inorganic, inert carrier materials. Recently, dissolution of the effective substances in low boiling point solvents and spraying of such active substance solutions by means of pressurized nitrogen has gained in significance. This type of preparation is marketed as aerosols.

As explained above, cationic or non-ionic surfactants may be added to the compounds of the invention. Suitable cationic compounds, for instance, are quaternary ammonium compounds such as cetyl pyridinium chloride or the large number of known benzalkonium chlorides. Adducts of ethylene oxide to compounds with acidic hydrogen, in particular to alcohols with chain lengths from 8 to 18 carbon atoms, which are known per se, can be used as non-ionic compounds.

The optimum pH value for the application of the invention is in the slightly acidic to neutral range and extends from about 4 to 8. Adequately weak organic acids, preferably acetic acid, are used to adjust the desired pH value. However, polyfunctional acids such as citric or lactic acid also are suitable.

The definition of the alkyl group $R^1$ as a straight-chain alkyl group with 8 to 18 carbon atoms, of $R^3$ as an alkyl group with 8 to 16 carbon atoms and of $R^2$ as a straight-chain alkyl group with 1 to 3 carbon atoms allows a large number of combinations. Now it has been surprisingly found that from such a multitude of microbiocidal compounds, a single one evidences extraordinary effectiveness against bacteria, fungi and yeasts, furthermore especially against spores. In addition, that compound is also very effective against algae. The high effectiveness of this compound transcends the scope of the properties which might be expected from the disclosure of U.S. Pat. No. 4,062,965.

The present invention therefore relates to 1,3-di-n-decyl-2-methyl-imidazolium chloride or bromide and further to a microbiocidal preparation composed of the above compound and a carrier. Accordingly it was the more surprising that this selected compound furthermore evidences pronounced sporicidal properties.

The preparation of 1,3-di-n-decyl-2-methyl-imidazolium chloride or bromide is performed in manner known from U.S. Pat. No. 4,062,965, in that for instance, 1-n-decyl-2-methyl-imidazole is reacted in a polar solvent with at least an equimolar amount of n-decyl chloride or bromide at temperatures between 80° and 150° C., and in that thereupon the solvent and any excess n-decyl chloride or bromide is removed. Suitable polar solvents in addition to water preferably are lower aliphatic alcohols, for instance i-propanol.

When using n-decyl chloride for the preparation of 1,3-di-n-decyl-2-methyl-imidazolium chloride, the effective substance is obtained in the form of a slightly light-brown powder with a softening point of 68° C. and a degree of purity of 95%. Recrystallization from acetic acid ethylester results in the chemically pure compound with a softening point of 82° C.

The effectiveness of the imidazolium salt of the invention is independent of its being in the form of a chloride or of a bromide. The comparison tests below were carried out using the chloride.

The evidence of microbiocidal effectiveness was shown in tabular form in U.S. Pat. No. 4,062,965, the test results on given test strains being shown depending on the concentration and time for a given effective substance at a predetermined pH. In order to show the patentability of the present invention even more clearly, the discussion below differs from that of the aforementioned patent and the limiting concentration of reliable effectiveness is listed for a predetermined time of action. A period of 10 minutes was selected as the time of action with due consideration to practice, as regards bacteria, fungi, yeasts and bacillus spores. The range of pH of the tested solutions of the effective substance in all reactions remains within the neutral range. The test results so obtained are representative because even when lowering or raising the pH limits, the same results and especially the same relations between the results are obtained.

The compound of the invention, i.e., 1,3-di-n-decyl-2-methyl-imidazolium chloride or bromide (III) was compared with the following compounds:
1,3-di-n-octyl-2-methyl-imidazolium chloride (IV)
1,3-di-n-dodecyl-2-methyl-imidazolium chloride (V)
1-n-dodecyl-3-n-octyl-2-methyl-imidazolium chloride (VI)

(a) Effectiveness against bacteria

The microbiocidal effectiveness of the tested compounds is ascertained by the suspension test according to the guidelines of the DEUTSCHEN GESELLSCHAFT FÜR HYGIENE AND MIKROBIOLOGIE (German Society for Sanitation and Microbiology), Gustav Fischer publisher, 1972, Stuttgart. The test germs used are Staphylococcus aureus, Escherichia coli, Proteus vulgaris and Pseudomonas aeruginosa.

| Test Strain | Limit Concentration of Effectiveness, in ppm Compound | | | |
|---|---|---|---|---|
| | III | IV | V | VI |
| S. aureus | 5 | 500 | 50 | 10 |
| E. coli | 10 | 500 | 500 | 50 |
| P. vulgaris | 5 | 100 | 100 | 50 |
| P. aeruginosa | 10 | 1000 | 500 | 100 |

(b) Effectiveness against fungi and yeasts

Similar to (a) the microbiological effectiveness is obtained according to the guidelines of the DEUTSCHEN GESELLSCHAFT FÜR HYGIENE & MIKROBIOLOGIE using the suspension test. The test germs used were Penicillum expansum, Aspergillus flavus, Trichophyton mentagrophytes, Microsporum gypseum, Candida albicans, Hansenula anomala and Geotrichum candidum.

| Test Strain | Limit Concentration of Effectiveness, in ppm Compound | | | |
|---|---|---|---|---|
| | III | IV | V | VI |
| P. expansum | 10 | 500 | 500 | 100 |
| A. flavus | 100 | 1000 | >1000 | 500 |
| T. mentagrophytes | 10 | 500 | 50 | 50 |
| M. gypseum | 10 | 500 | 50 | 50 |
| C. albicans | 5 | 500 | 50 | 10 |
| H. anomala | 5 | 500 | 500 | 50 |
| G. candidum | 1 | 100 | 10 | 10 |

(c) Effectiveness Against Spores

The spores of Bacillus subtilis and Bacillus cereus were used as test germs. Two nutrient agar plates were incubated at 37° C. for 10 to 12 days, each inoculated with the vegetative germs of B. subtilis and B. cereus, to prepare the spore suspension. The corresponding vegetative germs are elutriated each with 10 ml of sterile distilled water from the well grown plates, and the germ suspension is then centrifuged. The sediment is twice rinsed with sterile distilled water and then put in 5 ml of sterile water. The germ suspensions so obtained of B. subtilis and B. cereus are treated for 30 minutes at 80° C. in a water bath to kill the vegetative cells. Using the spore suspension so obtained, with a density of $10^6$–$10^8$ spores/ml, the sporicidal effectiveness of the compounds to be tested is ascertained by the generally known suspension test (see (a) and (b) ), the nutrient bouillon being reacted with an addition of 3% by weight of Tween ® 80 and 0.3% by weight lecithin to eliminate sporiostatic aftereffects. Tween 80 is an ethoxylated sorbitan oil acid ester, commercially available.

| Test Strain | Limit Concentration of Effectiveness, in % Compound | | | |
|---|---|---|---|---|
| | III | IV | V | VI |
| B. subtilis | 0.3 | 1.8 | >2 | 1.2 |
| B. cereus | 0.6 | >2 | >2 | 1.6 |

(d) Effectiveness against algae

Chlorella pyrenoidosa was used as the test strain. This algae strain is cultivated in 80 ml of a nutrient solution of the composition below
4.045 g $KNO_3$
2.340 g NaCl
0.110 g $CaCl_2$
1.235 g $MgSO_4$
0.010 g $MnCl_2$
0.007 g $ZnSO_4$
2.220 g $NaH_2PO_4$
0.890 g $Na_2HPO_4$
0.020 g $FeCl_3$
5 liters of distilled water,
while a mixture of carbon dioxide and air is passed through it. Following centrifuging, the grown algae from the nutrient solution, the algae sediment is placed into 20 ml of sterile tap water.

200 ml of the particular dilution of the algicide to be tested are each time placed into a 250 ml beaker. In parallel with these samples a control is kept with 200 ml of sterile tap water. Then 1 ml of the cultivated algae suspension is added to the individual beakers and the test set is allowed to stand at room temperature for 21 days. After this time, the amount of algae contained in each beaker is separated by filtration, dried and precisely weighed analytically.

The algicidal effectiveness of a substance is defined as the growth inhibition and computed as follows:

Growth inhibition = $100\% - 100(c-a)/(b-a)\%$ where
a = (dry weight of) inoculated algae amount, in mg
b = (dry weight of) growth in water without addition, in mg
c = growth in the dilution of the algicide, in mg

| | Results | |
|---|---|---|
| Substance | Amount of effective material in ppm | Growth inhibition in % |
| III | 2 | 32 |
| | 4 | 67 |
| | 8 | 95 |
| IV | 2 | 8 |
| | 4 | 42 |
| | 8 | 73 |
| V | 2 | 0 |
| | 4 | 6 |
| | 8 | 26 |
| VI | 2 | 12 |
| | 4 | 45 |
| | 8 | 65 |

These results show that the properties of the compound III of the invention transcend in an unexpected manner, both qualitatively and quantitatively, in effectiveness the range indicated in U.S. Pat. No. 4,062,965.

It will be obvious to those skilled in the art that many modifications may be made within the scope of the present invention without departing from the spirit thereof, and the invention includes all such modifications.

What is claimed is:

1. A microbiocidal composition comprising a carrier and a microbiocidally effective amount of 1,3-di-n-decyl-2-methyl-imidazolium chloride or bromide.

2. A process for killing microbes which comprises contacting said microbes with a microbiocidally effective amount of 1,3-di-n-decyl-2-methyl-imidazolium chloride or bromide.